United States Patent [19]

Briggs et al.

[11] Patent Number: 4,832,495
[45] Date of Patent: May 23, 1989

[54] APPARATUS FOR MEASURING OPAQUE MEDIUM COVERAGE OF A TRANSLUCENT SHEET

[75] Inventors: Daniel D. Briggs, Arvada; Peter Vischer, Golden, both of Colo.

[73] Assignee: Adolph Coors Company, Golden, Colo.

[21] Appl. No.: 107,962

[22] Filed: Oct. 13, 1987

[51] Int. Cl.$^4$ ............................................. G01B 11/28
[52] U.S. Cl. .................................... 356/379; 250/228; 356/236; 356/380
[58] Field of Search .................... 356/379, 380, 236; 250/228

[56] References Cited

U.S. PATENT DOCUMENTS

| | | | |
|---|---|---|---|
| 3,099,749 | 7/1963 | Williams | 356/379 |
| 3,968,363 | 7/1976 | Mielenz et al. | 250/228 |
| 4,461,568 | 7/1984 | Welbourn et al. | 356/236 |

FOREIGN PATENT DOCUMENTS

| | | | |
|---|---|---|---|
| 135597 | 5/1979 | German Democratic Rep. | 356/379 |
| 2178167 | 2/1987 | United Kingdom | 356/379 |

OTHER PUBLICATIONS

National Bureau of Standards Scientific Paper No. 447, Aug. 28, 1922, (vol. 18, 1922–1923), entitled "Theory, Construction, and Use of the Photometric Integrating Sphere," by E. B. Rosa & A. H. Taylor.

Seemuller et al, *IEEE Transaction on Instrumentation and Measurement*, vol. 1M-21, No. 2, May 1972.

*Primary Examiner*—F. L. Evans
*Attorney, Agent, or Firm*—Klaas & Law

[57] ABSTRACT

An apparatus for measuring the relative coverage of a predetermined portion of a sheet of translucent material with an opaque medium such as ink or photographic emulsion, comprising: a light source for providing a relatively constant intensity source of light over a predetermined measuring area; a positioning device for positioning the predetermined portion of the sheet of material to be measured over the predetermined measuring area of the light source; a light measuring device for measuring the relative amount of light from the light source which is transmitted through the predetermined portion of the sheet of material to be measured, whereby the relative amount of opaque medium coverage of the portion of the sheet to be measured is readily determinable by comparison of the measured amount of light transmitted through the predetermined portion of the sheet to be measured with predetermined calibration values.

1 Claim, 4 Drawing Sheets

APPARATUS FOR MEASURING OPAQUE MEDIUM COVERAGE OF A TRANSLUCENT SHEET

BACKGROUND OF THE INVENTION

The present invention relates generally to printing and package decoration and, more particularly, to an apparatus for measuring the ink, photographic emulsion, or other opaque medium coverage of a translucent sheet of material which has been provided with opaque artwork identical to that which is to be printed, in a particular color, on package material in a mass-production package printing operation.

In the high-speed production of packaging material, each color which is printed on a package is, in most cases, printed by a separate ink or dye on a separate printing roll or press. In order to determine the amount of ink that will be required for any particular packaging project, it is customary for the manufacture of the product which is to be packaged to furnish the package producer with separate transparencies having opaque portions corresponding to the artwork for each color to be printed, i.e. if three separate colors are to be printed on a package, the manufacturer would furnish the package producer with three separate transparencies, each showing the pring configuration for a particular color. The package producer computes the total area coverage for each separate color from the transparencies as a step in determining the total amount of ink of each color which will be required for the particular project. The task of determining the area coverage of a transparent sheet of material with opaque medium may be relatively simple, as when the artwork for a particular color consists of a few regular geometric shapes of constant density or intensity. However, when artwork consists of irregular shapes, such as alpha-numeric printing or the like, or of varying densities, the task of accurate area coverage estimation may range from quite time-consuming to nearly impossible. The conventional method for computing area coverage for irregular opaque shapes is to break the shapes down into a number of small, substantially regular figures, such as rectangles and triangles, and to then take the sum of the areas of these small regular figures. Due to the large number of computations and approximations that must be made using this method, it is not uncommon for a draftsman to spend the greater portion of a week estimating the area coverage of a single average-sized, e.g. 20 inches by 30 inches, sheet having complex artwork thereon. The large number of computations and approximations which must be made in estimating the area of complex artwork tends to make such an estimation process inaccurate because of the high risk of error in making the many computations and because of the inherent inaccuracy in approximating the area of certain irregular shapes using regular figures. When the artwork grades from transparent to opaque, accurate estimates are impossible. Estimation inaccuracies on the order of 20% to 25% are not uncommon. In a large production run, e.g. 1,000,000 packages provided on 20 inch by 30 inch carton blanks, a 20% overestimate of the coverage of a color which covers 80% of the package could result in the overpurchase of approximately 500 gallons of ink at a cost of approximately 2 dollars per gallon, resulting in a total unnecessary cost of approximately $1000 for that color, in addition to the cost involved in preparing the coverage estimate. Thus, it may be seen that a need exists in the packaging arts for an apparatus capable of quickly and accurately measuring the medium coverage of a transparency of the type provided to a package producer by a manufacturer.

SUMMARY OF THE INVENTION

The present invention may comprise an apparatus for measuring the relative coverage of a predetermined portion of a sheet of translucent material with an opaque medium such as ink which may be arranged in varying geometrical shapes and optical densities, comprising: (a) light source means for providing a relatively constant intensity source of light over a predetermined measuring area; (b) positioning means for positioning said predetermined portion of said sheet of material to be measured over said predetermined measuring area of said light source means; (c) light measuring means for measuring the relative amount of light from said light source means which is transmitted through said predetermined portion of said sheet of material to be measured, whereby the relative amount of opaque medium coverage of said portion of said sheet to be measured is readily determinably by comparison of said measured amount of light transmitted through said predetermined portion of said sheet to be measured with predetermined calibration values.

The present invention may also comprise an apparatus for determining the relative amount of opaque medium coverage of a translucent sheet of material comprising: an apparatus for determining the relative amount of opaque medium coverage of a translucent sheet of material comprising: light box means havng a relatively planar light transmitting surface for supporting the sheet of material thereon and for uniformly transmitting light through the portions of said sheet of material which are not covered by said opaque medium; light sealing enclosure means for light sealingly enclosing the sheet of material and said light transmitting surface of said light box means for preventing entry of light from light sources other than said light box means into said sealing means; cropping means operatively associated with said light box means and the sheet of material for preventing light transmission from portions of said light box means light transmitting surface other than the portion thereof covered by the sheet of material from entering said light sealing enclosure means; whereby substantially all light received in said light sealing enclosure means enclosing said light box means is initially transmitted through the sheet of material; light diffusion means positioned within said light sealing enclosure means for uniformly diffusing said light transmitted into said light sealing enclosure means and for preventing direct light transmitted through any portion of the sheet of material from entering a light intensity measuring means; light intensity measuring means operatively associated with said light sealing enclosure means and said light diffusion means for measuring the intensity of diffused light within said light sealing enclosure means; said measured light intensity being representative of the relative degree of coverage of the sheet of material with opaque medium.

The present invention may also comprise a method of determining the relative amount of opaque medium coverage of a predetermined portion of a sheet of translucent material comprising: directing light from a uniform, constant intensity light source area which is coextensive with the predetermined portion of the sheet to be measured onto one side of the sheet; measuring the amount of light from the light source that is transmitted through the sheet; comparing the measured amount of light to predetermined calibration values.

BRIEF DESCRIPTION OF THE DRAWING

An illustrative and presently preferred embodiment of the invention is shown in the accompanying drawing in which.

DETAILED DESCRIPTION OF THE INVENTION

The apparatus 10 of the present invention is used for measuring the relative coverage of a predetermined portion of a sheet of translucent material 11 with an opaque medium 13, such as ink. It will be understood that the "predetermined portion" of the sheet of translucent material may comprise the entire sheet of material or any smaller portion thereof which an operator may select. It will also be understood that "opaque medium" refers to anything contained in or on the sheet of otherwise translucent material which would prevent or partially impede light from being transmitted through the sheet of material. Thus, "portions of a sheet of translucent material covered with opaque medium" may refer to portions of a sheet of translucent material which are covered with opaque tape or the like, or may refer to portions of a sheet of translucent material which have been rendered optically dense or opaque by some machine process such as surface abrasion, etc., or may refer to portions of a sheet of translucent material covered by conventional ink and the like, etc.

In general, the apparatus 10 of the present invention comprises a light source means 12 for providing a relatively constant intensity source of light over a predetermined area which is at least as large as the area to be measured of the sheet of material; a positioning means 14 for positioning a predetermined portion (the entire sheet in FIGS. 1–5) of the sheet of material 11 to be measured over the predetermined measuring area of the light source means; a light measuring means 16 for measuring the relative amount of light from the light source means 12 which is transmitted through the predetermined portion of the sheet of material 11, whereby the relative amount of opaque medium coverage of the portion of sheet 11 to be measured may be determined by comparing the measured amount of light transmitted through the predetermined portion of the sheet 11 with predetermined calibration values. Light blocking means 18 are provided in operative association with the light measuring means 16 to ensure that only light passing through the predetermined portion of the sheet 11 to be measured is actually measured by the light measuring means. The light blocking means 18 may comprise sealing enclosure means 20 which prevents light other than light from the light source from entering the light measuring means. The light blocking means may also comprise cropping means 22 which are used for blocking off light from the light source means 12 other than light which passes through the portion of the sheet 11 to be measured. Coverage-calibration means 26, which may comprise a plurality of sheets of different known relative opacity, may be provided for calibrating the apparatus 10. Data processing means 30 may be provided for storing calibration values and for comparing measured light values associated with the light transmitted through the predeterined portion of the sheet 11 to be measured with the calibration values and/or for performing other functions.

Figure 1:
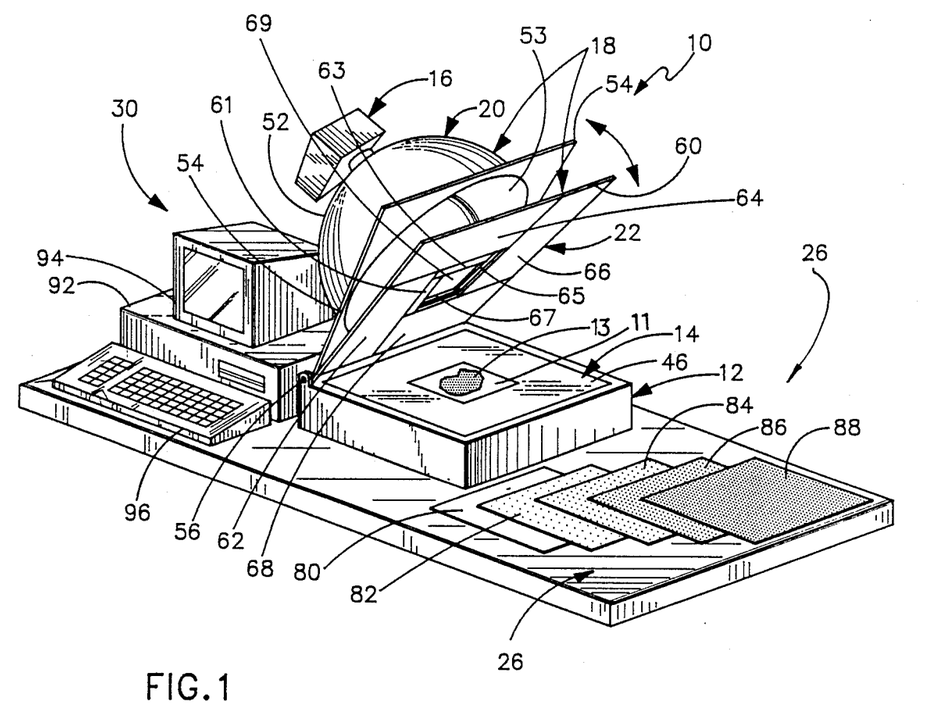
FIG. 1 is a partially opened perspective view of an apparatus for measuring the relative coverage of a sheet of translucent material with an opaque medium.
Figure 2:
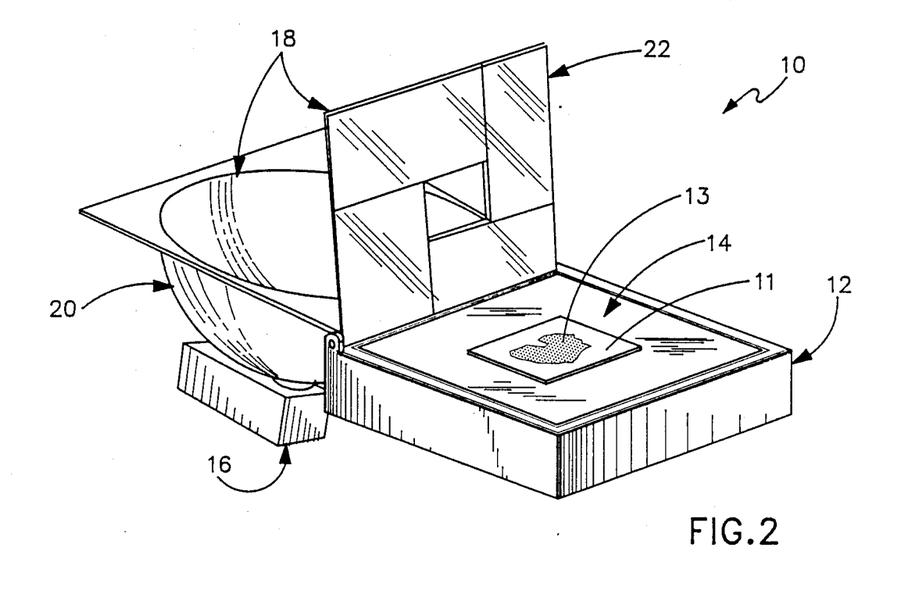
FIG. 2 is a perspective view of the apparatus of FIG. 1 illustrating the positioning of a sheet of translucent material with an opaque medium thereon above a light source.
Figure 3:
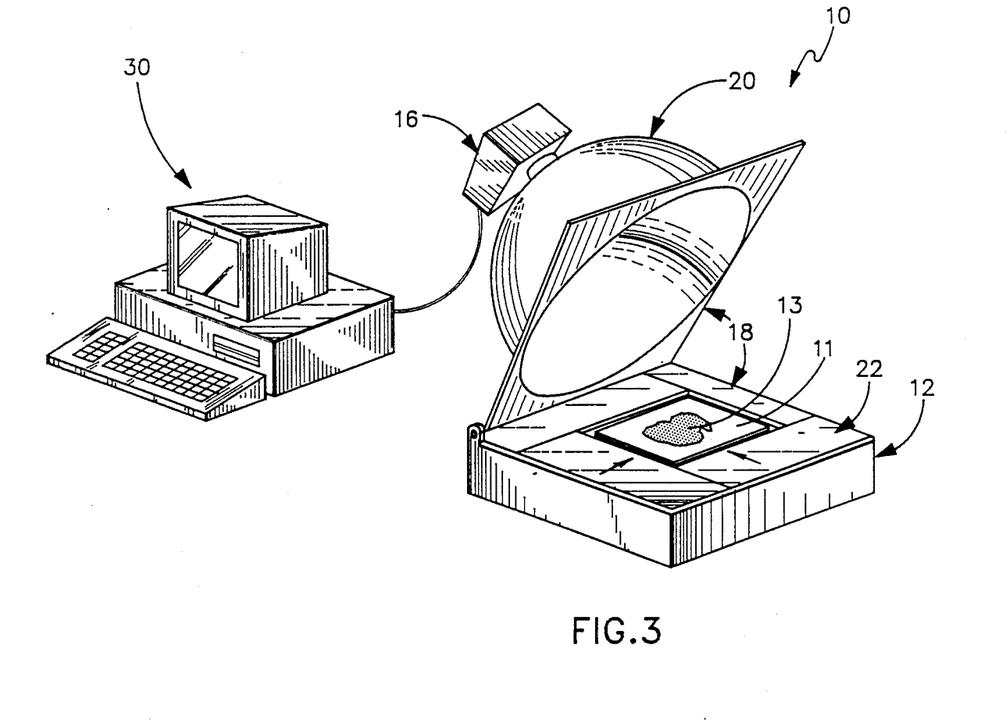
FIG. 3 is a perspective view of the apparatus of FIG. 1 illustrating the cropping of the total light source area to an area conforming to the shape of a sheet to be measured.
Figure 4:
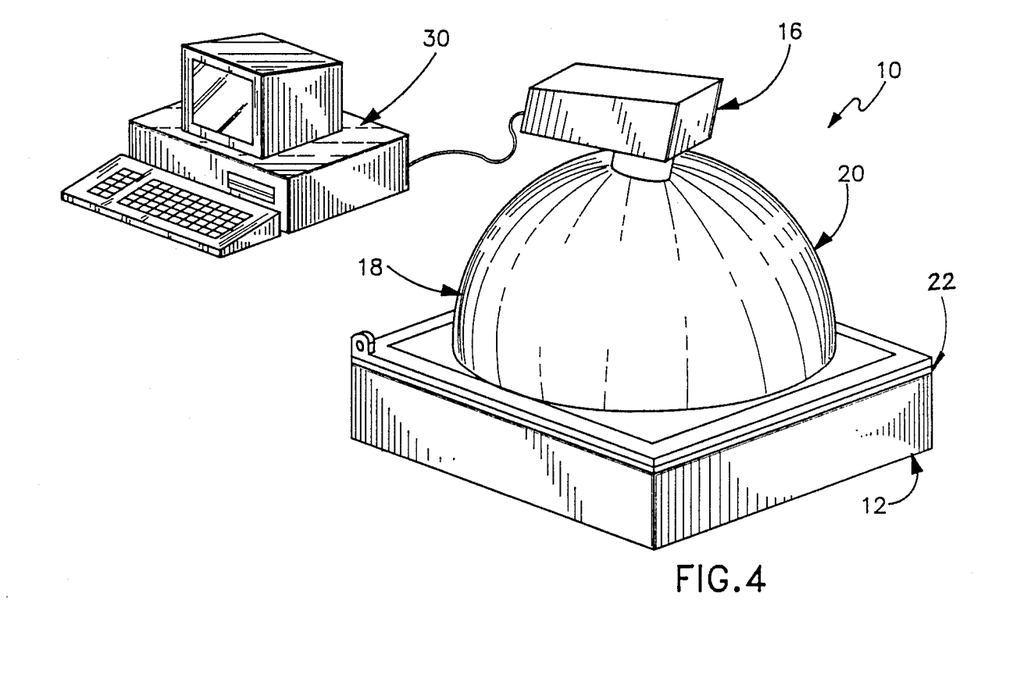
FIG. 4 is a perspective view of the apparatus of FIG. 1 illustrating the positioning of the apparatus for measuring of light passage through a sheet to be measured.
Figure 5:
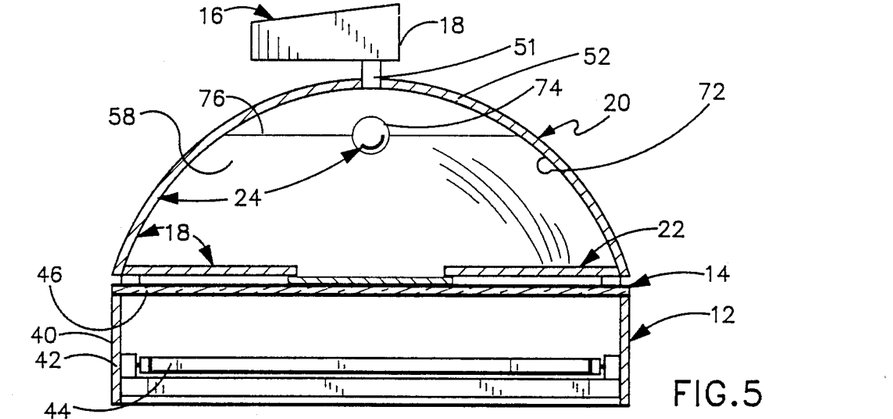
FIG. 5 is a cross-sectional view of the apparatus of FIG. 1 in the operating state shown in FIG. 4.

In operation, as illustrated in FIG. 2, a sheet of material 11 for which relative opaque medium 13 coverage is to be measured is initially positioned on the positioning means 14 above the light source 12. Next, as illustrated in FIG. 3, cropping means 22 are adjusted so as to block off transmisson of light from all portions of the light source 12 other than the portion positioned directly below the portion of the sheet of material 11 which is to be measured. Next, as illustrated in FIGS. 4 and 5, the sealing enclosure means 20 is positioned in enclosing relationship over the light source means, cropping means, and sheet 11 such that no light other than light from the light source enters the light measuring means 16. In the embodiment illustrated in FIGS. 1–5, a light diffusion means 24, FIG. 5, is operatively associated with the sealing enclosure means 20 and the light measuring means 16 in a manner such that only light which has passed through the portion of the sheet of material 11 to be measured and which has been diffused by the diffusion means enters the light measuring means. The measured intensity of the diffused light is proportional to the total "apparent open area" of the portion of the sheet of material 11 to be measured, i.e. the total area of the portion of the sheet of material to be measured minus the area thereof covered with opaque medium. Thus, the relative opaque mdium coverage is readily determined by comparing the measured light intensity associated with the portion of the sheet of material to be measured with calibration values determined by measuring equal-sized portions of sheets having known degrees of opacity, e.g. five sheets having opacities of 0%, 25%, 50%, 75%, and 100%, respectively. Having thus described the apparatus of the present invention and method of operation thereof in general, the invention will now be described in further detail.

As illustrated in FIG. 5, the light source means 12 may comprise a conventional light talbe 40 having an opaque enclosure box 42 with fluroescent lights 44 mounted therein. A translucent light-diffusing panel 46 is mounted in covering relationship with the open upper end of the box 42. In the embodiment of FIGS. 1–5, the positioning means 14 for positioning the translucent sheet of material 11 over the light source means 12 comprises the translucent panel 46.

The light measuring means 16 may comprise a conventional small-area light intensity measuring device such as a device sold under the product name PCT Digital Dot Area Meter, which is available from Tobias Associates, Inc. of 50 Industrial Drive, P. O. Box 2699, Ivyland, Pa., 18974–0347. The light intensity measuring device 50 is mounted on the sealing enclosure means 20 directly above a small hole 51 at the top thereof, FIG. 5.

As best illustrated in FIG. 1, sealing enclosure means 20 may comprise a hemisphere 52 fixedly mounted above the circular opening 53 in a rectangular mounting plate 54 having the same configuration as the translucent light panel 46 of the light table. The mounting plate 54 is in turn pivotally mounted on the light table by a conventional hinge assembly 56, enabling the sealing enclosure means 20 to move between the open position illustrated in FIG. 2 and the closed position illustrated in FIG. 4. Various peripheral sealing material such as felt, etc. (not shown) may be provided at the periphery of the sealing enclosure means 20 to increase the effectiveness of the light seal provided thereby. Thus, a light enclosure cavity 58, FIG. 5, is provided above the light source means 12 into which substantially no light enters other than light from the light source means.

As best illustrated in FIG. 1, cropping means 22 may comprise a conventional photographic diaphram-type cropping device 60 having a plurality of sliding plates 62, 64, 66, 68, 61, 63, 65, 67, which may be moved relative one another to provide a rectangular opening 69 of any desired rectangular configuration. The cropping device 60 is hingedly mounted to the light table by hinging assembly (not shown) having approximately the same pivot axis as the sealing enclosure means 20, enabling the cropping means 22 to be pivoted between an open position, as illustrated in FIG. 2, and a closed position, as illustrated in FIG. 3. This cropping device may alternatively (not shown) be hinge mounted from any of the remaining sides of 12.

As best illustrated in FIG. 5, light diffusing means 24 may comprise a smooth, white, light-diffusing surface 72 provided on the interior of hemisphere 52 such as by a flat or matte paint or the like. The light diffusing means also comprises a white, light-diffusing ball 74 which may be, e.g., a conventional white ping-pong ball or painted disc mounted on a support wire 76 attached to the interior wall of the hemisphere. The light-diffusing ball 74 is positioned directly below the opening 51 in the hemisphere 52 and sufficiently close thereto to diffuse any direct light from the light source 12 before it enters opening 51 whereby the light intensity measured by the light measuring means 16 is representative of the illumination of the entire enclosure 58 which is provided by all of the light transmitted through the portion of the sheet 11 to be measured, rather than being representative of direct light from a single portion of the sheet which may be positioned directly opposite hole 51.

As shown in FIG. 1, coverage-calibration means 26 may comprise a plurality of relatively large sheets having different degrees of opacity. For example, the coverage-calibration means may comprise a sheet 80 having 0% opacity, a sheet 82 having 25% opacity, a sheet 84 having 50% opacity, a sheet 86 havng 75% opacity, and a sheet 88 having 100% opacity. The relative opacity of the sheets is preferably provided by light filter material of different light densities. However, the different opacity sheets may also be provided by covering portions of translucent sheets with a uniform gridwork of lines of known width and spacing.

Data processing means 30 may comprise a conventional microcomputer or minicomputer 92, a conventional CRT display 94, and a conventional input terminal such as a standard keyboard 96. The output signal from 16 might also be directly processed by 92 on operator command.

Figure 8:
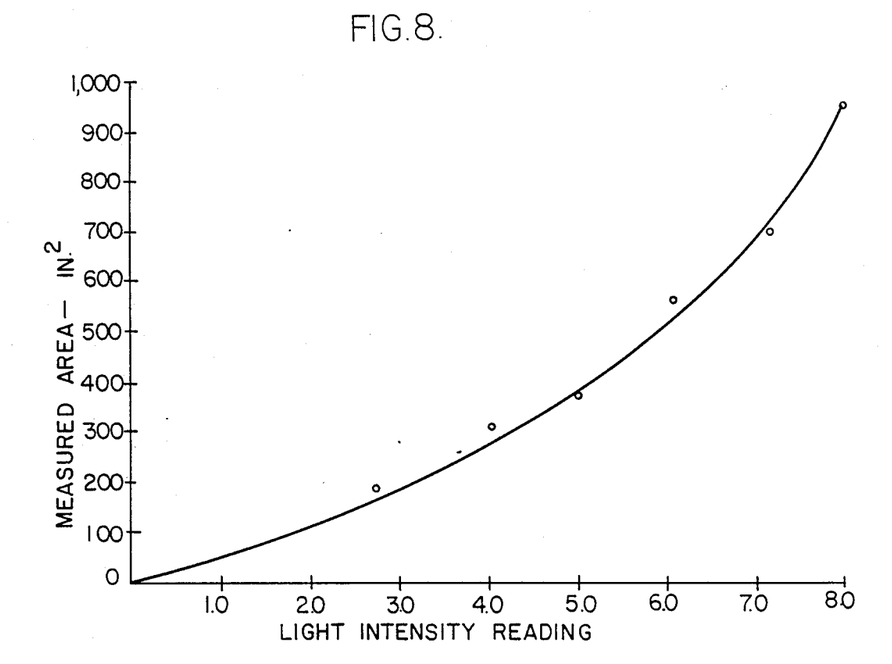
FIG. 8 is a size-calibration graph.
Figure 9:
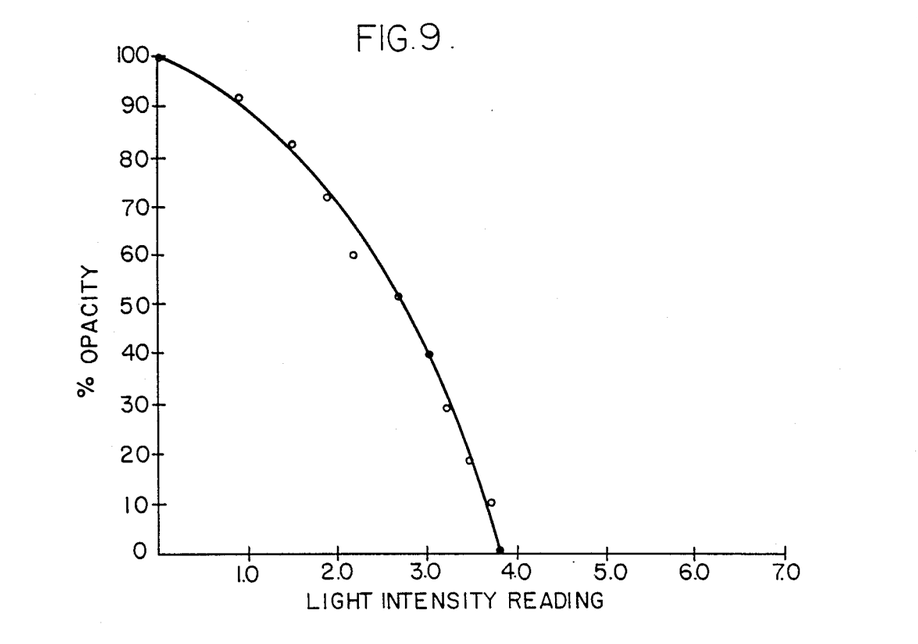
FIG. 9 is an opaque coverage-calibration graph.

One specific method for determining the opaque medium 13 coverage of a sheet 11 of transparent material of unknown area is as follows: Initially, a large sheet, which may be sheet 80, which is constructed of a material identical to the material from which sheet 11 and other sheets to be measured are constructed and which has no opaque medium thereon, is positioned in overlying relationship with the positioning means 14. Next, a number of differently-sized areas, which are to be used as area-calibration values, are selected. For example, for a light table panel having a total area of 1000 square inches, areas in 100 inch increments from 0 square inches to 1000 square inches may be selected. Next, for each selected area, cropping means 22 is adjusted to provide an opening 69 having that selected area and is positioned over the neutral density sheet 80 in the position illustrated in FIG. 3. Next, the sealing enclosure means 20 is positioned over the cropping means in the position illustrated in FIG. 4. Next, the intensity of diffused light within the enclosure 58 is measured with the light measuring means 16. Next, an ordered recording is made of the area-calibration values and the light measurement associated with each area-calibration value. In one embodiment, this ordered recording is made in the form of a size-calibration graph such as illustrated in FIG. 8, with the cropping area (the area of opening 69) used as one coordinate axis and the measured relative light intensity used as the other coordinate axis. Alternately, this information could be stored in machine-readable form in the form of a look-up table or least-squares fitted equation which is provided with an appropriate sofeware program for interpolating between data points on the look-up table or solving the equation. Next, the sheet of material for which opaque medium coverage is to be measured is mounted on the light box, as illustrated in FIG. 2. Next, as illustrated in FIG. 3, the cropping means 20 is adjusted to block off portions of the light table other than the portion thereof which is covered by the portion of the sheet of material for which opaque medium coverage is to be measured. In the embodiment illustrated, the portion of the sheet which is to be measured is the entire sheet. Next, the sealing enclosure means 20 is positioned over the sheet and cropping means, as illustrated in FIG. 4. Next, the intensity of diffused light within the enclosure 58 is measured by the light measuring means 16. Next, this measured light intensity is recorded either in human-readable form or, alternately, in machine-readable form. Next, the tested sheet is removed and a first one of the coverage-calibration sheets is mounted on the light table. The cropping means 22 is left in the same position, i.e. with the same-sized opening 69 as was used in cropping the sheet 11 to be measured, and is positioned over the coverage-calibration sheet in the manner as illustrated in FIG. 3. Next, the sealing enclosure means 20 is positioned over the cropping means and coverage-calibration sheet, as illustrated in FIG. 4, and a light measurement is made. This process is repeated for each of the coverage-calibration sheets, and the light measurement value associated with each different degree of opacity of the different coverage-calibration sheets is recorded in ordered form, e.g. by constructing a coverage-calibration graph with percentage of opacity as one coordinate and measured light intensity as the other coordinate as illustrated in FIG. 9, or, alternately, in a machine-readable form such as a look-up table or equation. Next, the light intensity measurement recorded for the sheet 11 to be measured is compared with the recorded light measurement values associated with the different opaque sheets, as by comparison to constructed opaque coverage-calibration graph, FIG. 9, to determine the relative coverage of the sheet of material with opaque medium. For example, if the light measurement value associated with the sheet 11 is equal to the light measurement value associated with the 25% opaque sheet, then the coverage of the sheet 11 with opaque medium 13 is 25%. Next, the light intensity measurement associated with the sheet of material 11 is compared to the area-calibration values, e.g. by comparison of the measured light intensity value to the size-calibration graph to determine the size of the uncovered area of the sheet 11. Alternately, a light reading from neutral density sheet 80 may be taken using the cropping means opening size used with sheet 11, and this light measurement value may then be compared to the size-calibration graph to determine the total area of sheet 11 directly. Next, the area of opaque medium coverage of the sheet 11 is determined from the determined relative coverage value and the determined uncovered sheet area or, alternately, the determined total sheet area. It will, of course, be appreciated that, if the area of the sheet 11 is known, then the necessity of measuring and recording different light intensity values for a size-calibration sheet and associated areas and determining the size of sheet 11 based on a comparison to those calibration values is obviated.

Figure 6:
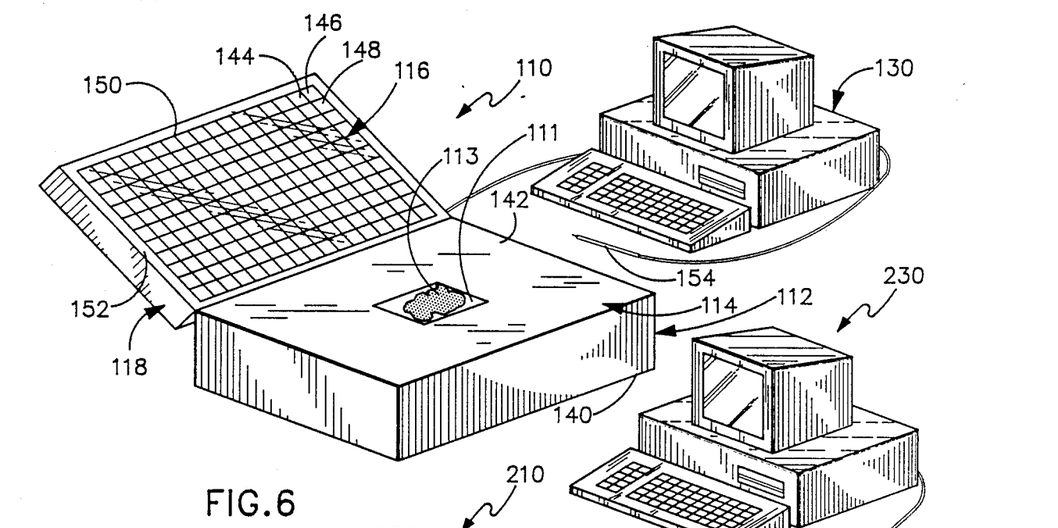
FIG. 6 is a perspective view of another embodiment of an apparatus for measuring the relative coverage of a sheet of translucent material with an opaque medium.

An alternate embodiment of an apparatus 110 for measuring the relative coverage of a predetermined portion of a sheet 111 of translucent material with an opaque medium 113 is illustrated in FIG. 6. Like the previous embodiment, the apparatus 110 may comprise a light source means 112 for providing a relatively constant intensity source of light over a predetermined measuring area; positioning means 114 for positioning a predetermined portion of a sheet of material 111 to be measured over a predetermined measuring area of the light source means; light measuring means 116 for measuring the relative amount of light from the light source means which is transmitted through the predetermined portion of a sheet of material to be measured; and light blocking means 118 for preventing light other than light from the light source which is transmitted through the predetermined portion of the sheet of material to be measured from entering the light measuring means. The apparatus may also be provided with data processing means 130 for storing measured data values and comparing measured data values to calibration values for determining the relative amount of coverage and/or the total area coverage of the sheet material 111 with opaque medium 113. The light source means may comprise a conventional light table 140, and the positioning means 114 may comprise a conventional translucent light table cover 142 which may be provided with a digitizing grid of the type used in many conventional computer-aided-design (CAD) systems. Light measuring means 116 may comprise a plurality of light measuring cells 144, 146, 148, etc., which are relatively small, e.g. squares measuring 0.2 inches on a side, and which are arranged in a rectangular gridwork 150 which is coextensive with the translucent light table cover 142. Each light measuring cell corresponds to a portion of the translucent light table cover and the corespondence of the portions of the light table cover and the plurality of light measuring cells is electronically stored in computer software in data processing means 130. Light blocking means 118 comprises the light cell gridwork 150 which is hinged to the light box and adapted to sealingly cover the light box when it is pivoted into opposite relationship therewith. A sealing peripheral edge 152 may be provided to improve the ability of the light cell gridwork 150 to block off light from light sources other than the light table. A cursor device 154 may be used in association with the digitizing grid provided in translucent light table cover 142 to cause only those cells in the light cell grid 150 which are positioned directly opposite to a sheet of material 111 to be operable. The cursor device 154 operates in combination with the digitizing grid in the same manner as the cursors and digitizing grids of conventional CAD systems, i.e. the cursor 154 is touched to the four corners of the sheet 111 to define the area from which light is to measured. Computer 130 processes this information and actuates only those cells in gridwork 150 which are positioned directly opposite the portion of translucent light table cover 142 which has been thus defined as a measuring area with cursor 154. Thus, in this embodiment of the invention, the cursor 154 and digitizing grid associated with the translucent light table cover and the computerized selection of cells in gridwork 150 act as an electronic cropping means for eliminating light from the light table other than light passing through the selected portion of translucent sheet 111 from being measured. In an alternate embodiment of this invention, the cursor device 154 may comprise a conventional "mouse-type" cursor device which must be initially touched upon a fixed reference point on the translucent light table cover 142 before being operable to define the four corners of the portion of sheet 111 to be measured. Both types of cursors are in common use and are well-known in the computer arts. The method of operation of the apparatus 110 of FIG. 6 may be identical to that described above with reference to FIGS. 1–4, except that the actual area of sheet 111 is readily determined by the computer through electronic computation based upon the reference points provided by cursor 154. It will also be appreciated that the coverage value for each light cell must be individually determined by comparison of the measured light intensity from that cell to calibration values to determine the relative coverage measured by that particular cell, and then the determined relative coverage of each of the cells is averaged to determine the total average coverage of the sheet 111.

Figure 7:
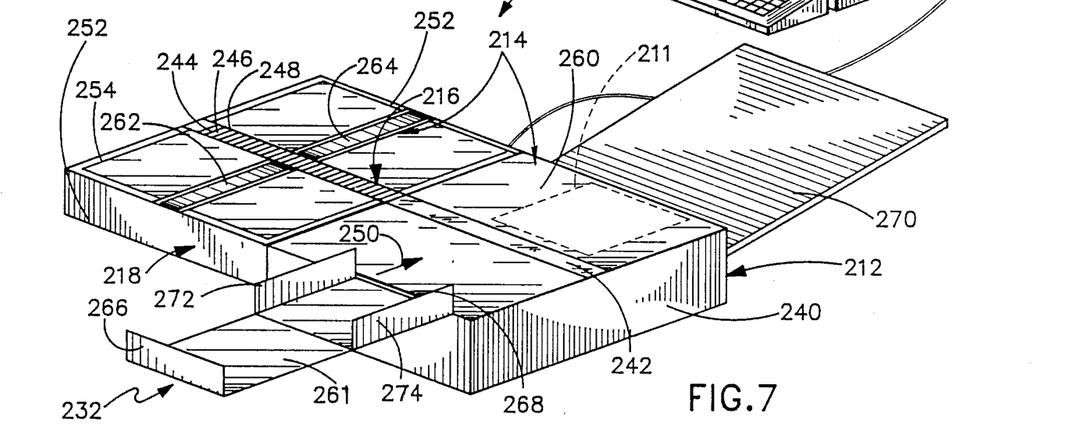
FIG. 7 is yet another perspective view of an apparatus for measuring the relative coverage of a sheet of translucent material with an opaque medium.

In yet another embodiment of the invention, as illustrated in FIG. 7, the apparatus 210 comprises a light source means 212, a positioning means 214, a light measuring means 216, a light blocking means 218, and a data processing means 230 which perform the same general functions as described above with reference to FIGS. 1–5 and FIG. 6. In this embodiment, sheet sizing assembly 232 is also provided which enables the size of a sheet to be quickly measured and electronically stored in computer 230. In this embodiment of the invention, the light source means 212 comprises a conventional light table 240 having a narrow transversely extending slit 242 at the center thereof which provides only a narrow band of light extending across the light table. The positioning means 214 comprises means for moving a sheet of material to be measured in a direction indicated at 250 which is perpendicular to the direction of extension of light slit 242. The positioning means comprises an opaque sheet support 260 over which a sheet of material 211, as indicated in phantom, passes. The positioning means also comprises a first belt drive 262 positioning in covering box 252 which is adpated to be located opposite a portion of sheet support 260 positioned upstream of light slit 242, and a second belt drive 264 mounted in covering box 252 and adapted to be positioned a portion of support sheet 260 locations downstream of light slit 242. The two belt drives operate in a manner similar to that of conventional copying machines to move a sheet of material 211 across the surface of support sheet 260 at a constant rate. Light measuring means 216 comprises a plurality of light cells 244, 246 arranged in a single cell width, narrow transverse band 248 which is positioned immediately above light slit 242 when bos 252 is pivoted into position above light table 240. Light blocking means 218 comprises covering box 252 in which the belt drives and light measuring means are mounted, which is hingedly attached to the light table by a conventional hinging assembly (not shown). A peripheral sealing strip 254 may also be provided to block out light other than light from the light table from entering the light measuring means. Sheet sizing assembly 232 comprises a horizontal support surface 261 which is provided with transversely adjustable members 272, 274, which may be spread apart or moved together into touching relationship with the edges of a sheet 211 positioned therebetween for determining the transverse dimension of the sheet. The sizing assembly 232 also comprises a longitudinally adjustable member 266 which may be moved forwardly and rearwardly to a position in touching engagement with the rear edge of a sheet 211 whose forward edge is engaged by transverse stop member 268. Sheet sizing assemblies are well-known in the copying machine arts. Infeed means (not shown) associated with a lower edge of stop member 268 enables a sheet of material 211 to be fed into moving engagement with first drive belt 262 through actuation of an infeed switch (not shown). The point in time at which the sheet of material is fed into the first drive belt 262, as well as the dimensions of the sheet, are electronically stored in the data processing means 230. Based upon these stored values, light measurement data from light cells 244, 246, etc., are stored by the central processing unit 230 only from measurements beginning at a point in time at which the leading edge of the sheet of material 211 to be measured is positioned in overlying relationship with light slit 242. Thereafter, the data signals from the light measuring cells 244, 246 are continuously monitored and stored until the trailing edge of the sheet passes over light slit 242. The data processing means may determine the occurrence of this trailing edge passage from the dimensions of the sheet 211 and the feed rate provided by belt drives 262 and 264. Based upon the electronically stored transverse dimension of the sheet, input signals from only those light measuring cells below which the sheet will pass are used; i.e. light measuring cells positioned transversely outwardly of the edges of the sheet 211 are electronically blocked off. In this embodiment of the invention, the light intensity of light passing through any portion of the sheet which is momentarily positioned above light slit 242 is measured directly by light measuring cells 244, 246, etc. The light intensity signal provided by each cell 244, 246, etc. is translated into a relative coverage signal by comparison of the measured light intensity value from each cell of predetermined calibration values. The coverage signal for each cell is then integrated in time between the first point in time when the sheet of material 211 began passage over the light slit and a second point in time when it ended passage over the light slit. This integrated value is then divided by the total amount of time between said first and second points in time to provide an average coverage value for each light cell. The average coverage value for all of the measuring light cells are then averaged to determine the average coverage value for the entire sheet 211. After passage across the support sheet 260, the sheet of material may be collected on a collection tray 270.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. A method of determining the area of opaque medium coverage of a sheet of translucent material of undetermined size comprising:
    (a) providing a relatively large size-calibration sheet which is constructed of material having substantially identical light transmitting properties to that of the sheet of material for which opaque medium coverage is to be determined, said size-calibration sheet having substantially no opaque medium thereon;
    (b) providing a plurality of coverage-calibration sheets having different, known degrees of opacity;
    (c) mounting said size-calibration sheet on a light table;
    (d) selecting a number of differently-sized areas to be used as area-calibration values;
    (e) blocking off light transmission from portions of said light table other than a portion thereof which is covered by said size-calibration sheet and which is equal to one of said selected differently-sized areas of step (d);
    (f) light sealingly covering the sheet mounted on the light table with an internally light diffusive enclosure;
    (g) measuring the intensity of diffused light within the enclosure;
    (h) repeating steps (e) through (g) for each of said selected differently-sized areas;
    (i) using the known area of each selected differently-sized areas and the associated measured light intensity value for each area, constructing a size-calibration graph with measured sheet area as one coordinate axis and measured light intensity as the other coordinate axis;
    (j) mounting the sheet of material for which opaque medium coverage is to be measured on the light box;
    (k) blocking off light transmission from portions of said light table other than the portion thereof which is covered by said sheet of material for which opaque medium coverage is to be measured;

(l) light sealingly covering the sheet mounted on the light table with the internally light diffusive enclosure;
(m) measuring the intensity of diffused light within the enclosure;
(n) recording the light intensity measurement thus obtained;
(o) mounting the size-calibration sheet on the light table;
(p) blocking off a portion of said size-calibration sheet which is identical to the configuration of the sheet of material for which opaque medium coverage is to be determined;
(q) light sealingly covering the sheet mounted on the light table with an internally light diffusive enclosure;
(r) measuring the intensity of diffused light within the enclosure;
(s) recording the light intensity measurement thus obtained;
(t) mounting one of said coverage-calibration sheets on the light table;
(u) blocking off a portion of said coverage-calibration sheet which is identical to the configuration of the sheet of material for which opaque medium coverage is to be determined;
(v) light sealingly covering the sheet mounted on the light table with an internally light diffusive enclosure;
(w) measuring the intensity of diffused light within the enclosure;
(x) repeating steps (t) through (w) for each of said coverage-calibration sheets;
(y) using the known degree of opacity for each coverage-calibration sheet and the measured light intensity value for each sheet, constructing an opaque coverage-calibration graph with degree of opacity as one coordinate and measured light intensity as the other coordinate;
(z) comparing the light intensity measurement recorded in step (n) to the opaque coverage-calibration graph to determine the relative coverage of said sheet of material with opaque medium;
(aa) comparing the light intensity measurement of step (s) to the size-calibration graph to determine the area of said sheet of material;
(bb) computing the area of opaque medium coverage of said sheet from the determined relative coverage of step (z) and the determined sheet area of step (aa).

* * * * *